United States Patent [19]

Clark, Jr.

[11] 4,401,122
[45] Aug. 30, 1983

[54] CUTANEOUS METHODS OF MEASURING BODY SUBSTANCES

[75] Inventor: Leland C. Clark, Jr., Cincinnati, Ohio

[73] Assignee: Children's Hospital Medical Center, Cincinnati, Ohio

[21] Appl. No.: 63,159

[22] Filed: Aug. 2, 1979

[51] Int. Cl.³ .............................................. A61B 5/00
[52] U.S. Cl. .................................. 128/635; 128/636; 128/632
[58] Field of Search ....................... 128/635, 260, 633; 356/41, 417, 427; 422/68; 23/230 LC

[56] References Cited

U.S. PATENT DOCUMENTS

| | | | |
|---|---|---|---|
| 3,795,239 | 3/1974 | Eberhardt et al. | 128/635 |
| 3,958,560 | 5/1976 | March | 128/633 |
| 3,960,753 | 6/1976 | Larrabee | 23/230 LC |
| 4,003,707 | 1/1977 | Lübbers et al. | 128/633 |
| 4,034,756 | 7/1977 | Higuchi et al. | 128/260 |
| 4,215,940 | 8/1980 | Lübbers et al. | 356/41 |
| 4,240,438 | 12/1980 | Updike et al. | 128/635 |
| 4,255,053 | 3/1981 | Lübbers et al. | 356/417 |
| 4,269,516 | 5/1981 | Lübbers et al. | 356/427 |
| 4,272,484 | 6/1981 | Lübbers | 422/68 |
| 4,306,877 | 12/1981 | Lübbers | 128/633 |

Primary Examiner—Richard J. Apley
Assistant Examiner—T. J. Wallen
Attorney, Agent, or Firm—Wood, Herron & Evans

[57] ABSTRACT

Cutaneous methods for measurement of substrates in mammalian subjects are disclosed. A condition of the skin is used to measure a number of important substances which diffuse through the skin or are present underneath the skin in the blood or tissue. According to the technique, an enzyme whose activity is specific for a particular substance or substrate is placed on, in or under the skin for reaction. The condition of the skin is then detected by suitable means as a measure of the amount of the substrate in the body. For instance, the enzymatic reaction product or by-product of the reaction is detected directly through the skin as a measure of the amount of substrate. Polarographic electrodes or enzyme electrodes are employed as skin-contact analyzers in the transcutaneous measurement of oxygen or hydrogen peroxide to quantitatively determine blood substances such as glucose and alcohol. In a preferred quantitative technique, the skin is arterialized, i.e., heated or otherwise treated to arterialize the skin capillaries when the measurements are made. Colorimetric detection methods are also employed.

37 Claims, 3 Drawing Figures

ENZYMATIC TRANSCUTANEOUS GLUCOSE MEASUREMENT

ENZYMATIC TRANSCUTANEOUS GLUCOSE MEASUREMENT

CUTANEOUS METHODS OF MEASURING BODY SUBSTANCES

BACKGROUND OF THE INVENTION

Instruments capable of continuously indicating the chemical composition of blood have proved to be useful in regulating operative and postoperative managements of patients, and in teaching and research. At first, such instruments were used with sensors mounted directly in the extracorporeal blood circuit that is used for perfusion of open-heart surgery patients. Later, continuous monitoring of both machine and patients was conducted by means of continuous withdrawal of blood pumped into external cuvettes equipped with appropriate sensors. Satisfactory systems are now provided for a rapid and accurate measurement of blood composition such as pH, $pCO_2$ and $pO_2$.

In addition to the analytical techniques mentioned above, oxygen and carbon dioxide have been measured on the skin by virtue of their diffusing through it. Recently, the continuous monitoring of blood oxygen by a heated electrode positioned on hyperemic skin has been accomplished. Substances such as halogenated organic compounds, particularly fluorinated compounds, have also been found to diffuse through the skin and have been measured. For instance, with reference to U.S. Pat. No. 3,911,138, quantitative measurements have been made of skin-diffused fluorinated compounds by gas chromatography and electron-capture detectors.

Other techniques have been employed for measuring biological substances in the blood. For instance, ethanol is currently measured in blood, either directly or by a breath sampling, by classical chemical, gas chromatographic and enzyme methods. One of the alcohol enzyme methods depends upon the polarographic measurement of hydrogen peroxide, while others depend upon the consumption of oxygen. However, none of these methods readily lend themselves to continuous monitoring.

In brief, while there are a variety of techniques available for the measurement of blood gases and other substances, new methods are desired which more readily lend themselves to continuous monitoring or enable the measurement of key biological substances.

SUMMARY OF THE INVENTION

This invention is directed to a new method for cutaneously measuring substances in the body. The method is conducted by contacting the substrate through the skin of a mammal with an enzyme selective for the substrate being analyzed, then reacting the substrate with the enzyme and directly detecting a condition of the skin as a measure of the amount of substrate. The procedure is completely non-invasive or is non-invasive after one implant.

In a most preferred embodiment, the skin is arterialized and the enzyme is reacted with the substrate in the blood at or near the skin surface. A condition of the reaction is detected such as the amount of oxygen consumed, or hydrogen peroxide or carbon dioxide by-products, as a measure of the amount of substance. The skin capillaries may be arterialized by heating or chemical treatment.

It has been discovered that biological substances which do not diffuse from the blood through the skin may still be measured according to this invention. For instance, one of these substances is glucose. In accordance with one preferred technique of this invention, a substance such as glucose under the skin may be measured by means of a skin-contact oxygen electrode, particularly a heated electrode. This electrode is sometimes referred to herein simply as a transcutaneous oxygen electrode or $tcpO_2$ electrode. The heat arterializes the capillaries in the skin, that is to say, the blood in the skin is brought into equilibrium with the blood in the arteries. Quantitative measurements may then be made. In this method, glucose oxidase is placed just beneath the dermis where it catalyzes the consumption of oxygen according to the amount of glucose available, as expressed by the equation:

$$GLUCOSE + OXYGEN \rightarrow GLUCONIC\ ACID + HYDROGEN\ PEROXIDE$$

The glucose diffuses to the implanted enzyme where it is oxidized and the resultant decrease in oxygen is sensed by the electrode placed over or near the enzyme site. The gluconic acid diffuses away from the site to be picked up by the blood or the lymphatic stream. The hydrogen peroxide also diffuses away, or may be decomposed by local catalase activity. Should hydrogen peroxide be a problem, it can be destroyed by incoporating catalase with the glucose oxidase. Thus, in accordance with this embodiment, the skin condition being detected is a resultant decrease in oxygen in the skin layer as a measure of the amount of glucose in the blood under the skin.

In an alternative embodiment, the enzyme may react with a substance to produce by-product hydrogen peroxide which may then be sensed by a hydrogen peroxide sensitive electrode. For instance, an $H_2O_2$ polarographic anode may be employed to detect subdermal components. Thus, a transcutaneous $tcpO_2$, $tcpH_2O_2$, or even a $tcpCO_2$ electrode may be employed as the skin condition analyzer.

In addition to positioning polarographic electrodes on hyperemic skin to detect oxygen in a local subdermal oxygen sink or by-product hydrogen peroxide, other procedures for quantitation of the substrate may be employed. For instance, a colorimetric method may be used for detecting amounts of hydrogen peroxide produced by enzymatic reaction. The amount of hydrogen peroxide produced may be measured by a system which comprises a chromogenic reagent or reagents capable of undergoing a color change in the presence of hydrogen peroxide, the amount of hydrogen peroxide present being measured by colorimetrically measuring the color change. One known method of doing this is by means of a quadravalent-titanium and xylenol orange which react to form a stable red color with hydrogen peroxide (Taurnes & Nordschow, Amer. J. Clin. Path., 1968, 49, 613). Reference may be had to this article for details or to U.S. Pat. No. 3,907,645 suitable reactants. The amount of hydrogen peroxide produced is measured by the intensity of the color.

Furthermore, an enzyme reactant may be tattooed in the skin. In this form an enzyme or a detector of the enzyme reaction may be immobilized in the skin and a color change or a condition of the skin may be visually observed or measured.

The reaction of the enzyme with the substance being measured may also be followed through the skin by measuring the electrons which are removed during the enzymatic reaction and transferred, for instance, to a colored dye. For example, lactic acid will undergo an enzymatic reaction with lactic acid dehydrogenase. In this reaction, electrons are removed from the acid and are available for transfer to a colored dye which intensifies and the amount of the lactic acid is measured by intensity of the color.

Therefore, in its broader aspect, this invention is directed to the cutaneous measurement of a corporeal substance by reacting an enzyme with the substance anywhere across the layer of skin and detecting a condition of the skin as a measure of the amount of the substance. The enzyme may be placed on, in or under the skin in accordance with any particular technique. In one particularly preferred form, the enzyme is implanted below the skin. The implantation allows for continuous monitoring of the substance under examination. For instance, it has been shown that a subdermal glucose oxidase may be implanted and does in fact interact with glucose to produce a local oxygen sink which is measurable with a tcpO$_2$ electrode. The intensity and extent of the oxygen sink in the presence of a given flux of glucose is dependent upon the geometry of the implant and the activity of the enzyme. Both of these can be controlled. The exact nature of healing, fibrous tissue invasion and capillary new growth following implantation cannot, of course, be controlled but, the implantation can be regulated with satisfactory practical limits. The tissue reaction to such implants in humans after many months has been small and they are easily replaced and removed. The sensing of glucose via oxygen in this way may be accomplished by relating the difference in the polarographic oxygen current between the normal skin and the enzyme modulated skin. For instance, reference may be had to my earlier patents, namely U.S. Pat. Nos. 3,912,386; 3,380,905 and 3,539,455 for specific electrode structures which may be used to detect oxygen and H$_2$O$_2$. Using devices of the type mentioned in my patents, a dual electrode system may be used to sense glucose by relating the difference in polarographic oxygen current between the normal skin and the enzyme modulated skin. In another form, a single electrode system can be employed. For instance, polarographic anodes of the types described in my U.S. Pat. No. 4,040,908 may be employed to measure hydrogen peroxide by-product as a measure of the substrate.

In one form of procedure, the enzyme is dissolved in water and injected just under, or into, the skin and a tcpO$_2$ electrode is positioned on the skin and secured just over the enzyme site. The temperature of the skin is controlled at approximately 38°-44° C. In another procedure, enzyme powder has been mixed with silicone or fluorocarbon oils before subcutaneous injection. Enzyme has also been mixed with silicone monomer and converted with suitable catalyst to a thin rubber-like polymer sheet about half the size of a postage stamp which is then implanted through an incision in the skin. Such implants heal rapidly and retain enzyme activity for many days or weeks and probably much longer. Enzyme implants have been made using a thin sheet of reinforced Silastic (organosilicone polymers, Dow Corning subdermal implant No. 501–1.007 in. thick) coated with enzyme, immobilized by treatment with glutaraldehyde solution and drying in the cold. Enzyme, either free or immobilized has also been trapped between two layers of cellophane, cuprophan or collagen just before implantation.

Therefore, various modes of cutaneous treatment, including implantation, and devices for achieving same, may be employed in accordance with the principles of this invention. Skin implants may be very small, perhaps a sphere with a minimum dimension of about 1 mm in diameter. Patients who require continuous monitoring, such as diabetics may be provided with a skin implant and their condition may be continuously monitored by any of the aforementioned detection techniques. Furthermore, in another form, the encapsulated enzyme is embodied below the surface of the skin in such a way that it is visible. A dye may be added thereto such that a change in color is effected when the glucose reaches a certain value. Redox dyes directly coupled or indirectly coupled through an emzyme-glucose reaction could be used. Such devices would give a warning signal to a diabetic.

Also, there are some substances which form in the body and enter the blood when hypoxia is present. Hypoxanthine is one. Using a tcpO$_2$ electrode and xanthine oxidase EC1.2.3.2., one could have an hypoxia warning device which fastens to the skin and warns of the presence of this substance by virtue of $\Delta$pO$_2$ over normal skin and skin with a xanthine oxidase implant.

This invention and its numerous advantages along with other embodiments will be exemplified with reference to the drawings and the following experiments.

I—EXPERIMENTS

Figure 1:
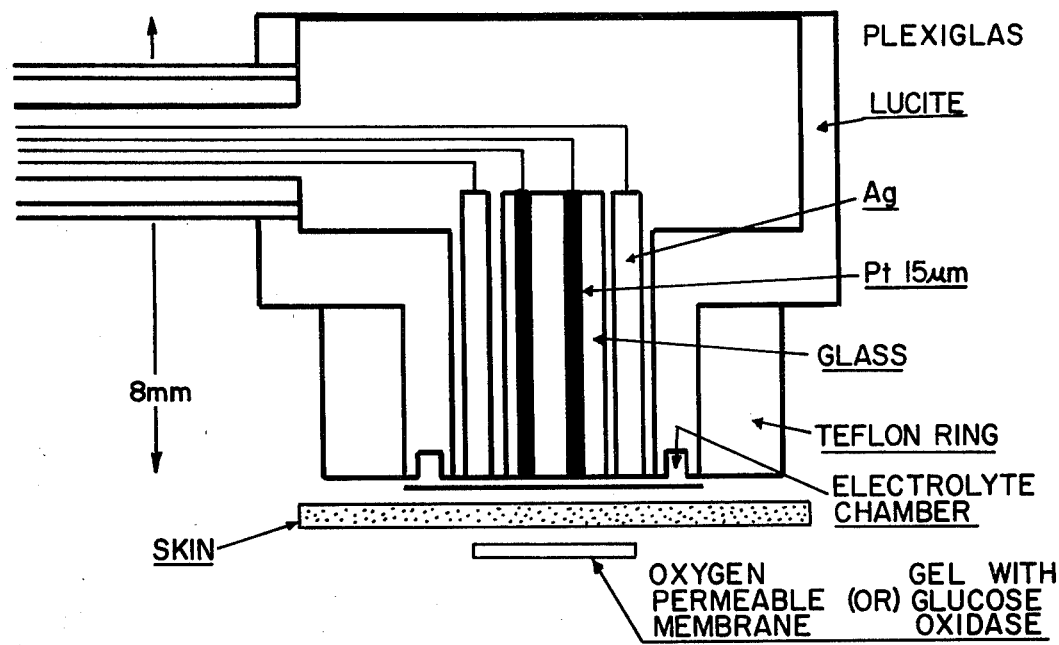
FIG. 1 illustrates a typical transcutaneous electrode arrangement for detecting skin oxygen content as a measure of the substrate.

An electrode of FIG. 1 was employed in these experiments in the measurement of glucose. The overall arrangement of the circuit and polarographic cell may be obtained with reference to my above mentioned patents. Such devices are well known. Their structures or their operation per se need not be detailed here.

The transcutaneous pO$_2$ in air breathing cats was measured with the electrode at about 38°-44° C. The measurement of oxygen transcutaneously depends upon the fact that this gas readily leaves the capillary blood and diffuses through the skin to the outside. By heating the skin to approximately 38°-44° C., the capillary vessels in the blood stream dilate, the skin becomes red and the amount of oxygen that is diffused from the skin increases and in fact comes into equilibrium with arterial blood. Hence, the pO$_2$ of an air breathing animal on the surface of the skin is on the order of magnitude of about 80 mm of Hg. (A of FIG. 2). Following the breathing of oxygen, this transcutaneous pO$_2$ may increase to the region of 150 mm or so shown. This procedure was followed by insertion of glucose oxidase in different forms underneath the surface of the cat's skin. With reference to FIG. 1, any of the forms of injection or implantation discussed above may be used. Then, the transcutaneous pO$_2$ was remeasured. The difference or $\Delta$-pO$_2$ is a reflection of the blood glucose content.

Figure 2:
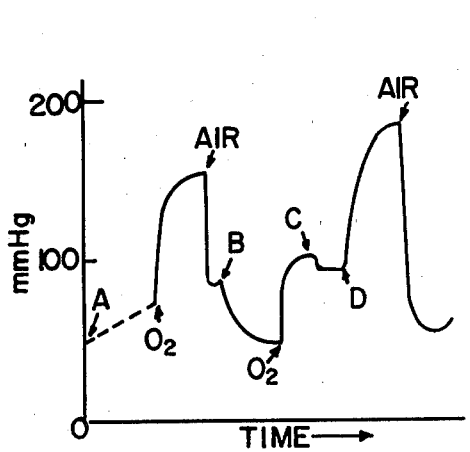
FIGS. 2 and 3 are charts illustrating measurements of glucose and ethanol with a transcutaneous pO$_2$ electrode.

With reference to FIG. 2, the effect of increasing and decreasing blood glucose levels is illustrated. After returning from oxygen to air breathing, there was a prompt fall in the tcpO$_2$. Then, beginning at a few seconds after the injection of glucose (B) (10 cc of 5% was given intravenously), there was a further oxygen decrease. Breathing of oxygen a few minutes after the injection results in an increased, but to a much lower average tcpO$_2$, than breathing oxygen before. Then, a glucose injection (C) decreased the tcpO$_2$. After the injection of glucose oxidase (D) which converts the circulating glucose to gluconic acid, while the cat was still breathing oxygen, the tcpO$_2$ increased to the highest point measured. On return to air breathing, the level of the tcpO$_2$ dropped. The tcpO$_2$ response to oxygen was greatly decreased when glucose was given. Both of the abrupt falls in tcpO$_2$ following oxygen breathing were obtained after returning the animal to air breathing.

In this series of experiments, no attempt was made to perfectly quantitate the result but to demonstrate the principle of the skin sensing electrode, namely increasing amounts of glucose in the blood are reflected by a decreasing transcutaneous pO$_2$. Further evidence that the initial Δ-pO$_2$ was a reflection of glucose was found by injecting the enzyme glucose oxidase directly into the bloodstream of the cat. When the purified enzyme was injected this way, there was a prompt increase in the tcpO$_2$ leveling off at a certain value, thus demonstrating that the initial reading was due to glucose since the enzyme when injected intravenously converts all the glucose to gluconic acid.

II—EXPERIMENTS

In another set of experiments, glucose oxidase was mixed with a silicone preparation and then a catalyst was added. The material was then pressed between two glass slides to produce a thin film of silicone rubber having glucose oxidase embedded in it. When this membrane was hardened, it was placed subcutaneously in a cat and healed in a perfectly normal manner after a few days. Immediately after implantation, there was a difference detected by the electrode of FIG. 1 in the Δ-tcpO$_2$ between the normal skin and the enzyme treated skin. It had previously been demonstrated that glucose oxidase mixed with the polymerizable silicone is active in the oxidation of glucose to gluconic acid. In another preparation, glucose oxidase was mixed with silicone oil and this was injected subcutaneously. Still in another form of implantation, the glucose oxidase was mixed with fluorocarbon liquid and injected subcutaneously. In still another form, a glucose oxidase was trapped between a thin layer of Silastic reinforced (artificial skin) and a layer of collagen. In each form, the method of this invention was established, namely that the amount of glucose could be detected by measuring the difference in Δ-tcpO$_2$.

III—EXPERIMENTS

Figure 3:
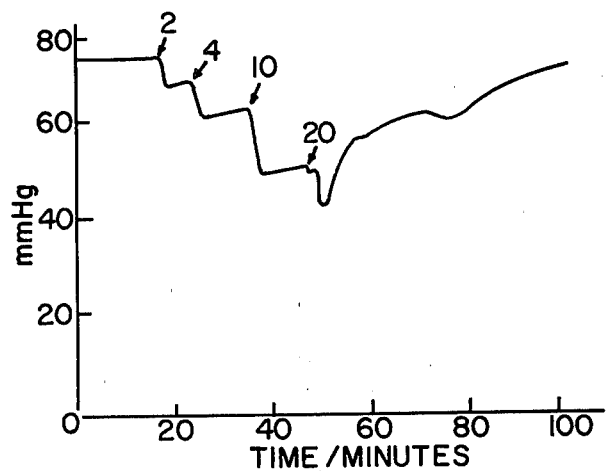

In another set of experiments, an oxygen-consuming alcohol oxidase was placed on the skin of an anesthetized cat. The animal was anesthetized with sodium pentobarbital and maintained at 38° C. with an infrared heater modulator modulated by a rectal thermistor signal. The electrode was fastened to the shaved skin just below the thorax. A few crystals of the oxidase preparation in about 50 μl of water (215 mg/50 μl) was placed on the skin and the electrode was set in place. After a stable reading was obtained, alcohol solution was injected. The results are shown in FIG. 3 and numbers referred to at the points of injection, namely 2, 4, 10 and 20, are the number of milliliters of 10% ethanol given intravenously. The measurements of the circulating ethanol were employed using a transcutaneous tcpO$_2$ electrode of the type shown in FIG. 1. With reference to FIG. 3, it is demonstrated that increasing amounts of alcohol decreased the tcpO$_2$ step-wise and that recovery toward the initial value occurred over the following minutes. The less than expected effect of the 20 milliliter dose was not understood, but may possibly be due to a pharmacological affect on the skin or possibly an acute drop in blood pressure.

Other means of performing the experiments of the above type involving volatilizable components, such as alcohol, include the incorporation of the enzyme in the electrode's electrolyte, immobilizing it on the membrane, and the use of two cathodes, one coated with enzyme and one uncoated. As mentioned above, one may also have a coated and an enzyme-free spot on the skin and calibrate by measuring the pO$_2$ versus blood or end tidal alcohol. The temperature control required for the tcpO$_2$ measurement is ideal for stabilizing enzyme activity. Enzyme would be best dissolved in a buffer with suitable coenzymes and stabilizing agents. There are several alcohol oxidases and dehydrogenases with varying specificity toward alcohols of different chemical structures, but all respond to ethanol for use in Experiments III. Of course, the tcpO$_2$ skin procedure above discussed with reference to alcohol can be used for the continuous measurement of other volatile enzyme substrates where oxygen depletion is utilized in their measurement.

In view of the above experiments, it is obvious that a number of other enzymes can be used in order to detect and measure a substance transcutaneously. The following Table is a listing of the enzymes, their identifying number, source and typical substrates with which they may react for measurement in accordance with the principles of this invention. t,0130

Any enzyme may be used which, in the process of catalyzing the reaction with its substrate or substrates directly or indirectly, consumes or requires oxygen.

Using the international nomenclature of the enzyme commission (see for example T. E. Barman Enzyme Handbook, Vol. 1, 2, and Supplement, Springer-Verlag, New York 1969), classes of enzymes can be described which will be useful in this invention. Since new enzymes are discovered each year, examples of presently known enzymes can be used to illustrate the principles involved. There are six main classes:

1. Oxidoreductases
2. Transferases
3. Hydrolases
4. Lysases
5. Insomerases
6. Ligases Most of the oxygen consuming enzymes are in Class 1. If such enzymes may use molecular oxygen directly, they are then called oxygen oxidoreductases, or if indirectly, through a "coenzyme" or "cofactor" which is reduced by the enzyme and reoxidized by molecular oxygen, they are simply called oxidoreductases.

Class 1, the oxidoreductases, are divided into subclasses, for example, 1.1 are those acting on the CH—OH group of donors. Class 1.1 is divided as follows:

1.1.1. with NAD or NADP as acceptor
1.1.1. with cytochrome as acceptor
1.1.3. with oxygen as acceptor
1.1.99 with other acceptors Glucose oxidase, an oxygen oxidoreductase acting on the CH-OH group of donors is therefore 1.1.3. Glucose oxidase is a 1.1.3. enzyme and is key numbered as 1.1.3.4., galactose oxidase is 1.1.3.9. If glucose is oxidized by a "dehydrogenase" enzyme, it is called glucose dehydrogenase:

Glucose+NAD(P)=Gluconolactone+reduced NAD(P)

It is classed as 1.1.1.47.

Galactose dehydrogenase uses NAD, rather than NADP, as a cofactor:

Galactose+NAD=Galactolactone+reduced NAD (or "NADH")

These two dehydrogenases do not consume oxygen directly but via cofactors. The dehyrogenase reaction stops when all the cofactor is used up by reduction to NADH or NADPH. The NADH or NADPH can be reoxidized to NAD or NADP by a number of means, including oxidation by another cofactor, by a platinum anode, or by oxygen. Hence, the glucose substrate, the donor molecule, is oxidized by oxygen, indirectly.

Other natural cofactors, such as cytochrome or synthetic substances, can act as cofactors with the final result that a specific substrate is oxidized with the stoichiometric consumption of molecular oxygen.

The other five main classes of enzymes can be used in conjunction with the oxidoreductases, or oxygen-consuming dehydrogenases, to expand the range of analysis. Examples could be found to illustrate a reaction for each of the main classes of 2, 3, 4, 5 and 6.

A Class 2 example is dextransucrase (EC2.4.1.5) which catalyzes the reaction of low molecular weight dextran with sucrose to give a larger dextran polymer. It consumes sucrose and yields fructose. Hence, depending on conditions, it could be used to measure dextran or sucrose.

A Class 3 example is sucrase, commonly found in yeast, which is a beta-fructofuranoside and is a hydrolase. It is EC3.1.1.2. which splits sucrose into fructose and glucose. With glucose oxidase, it could be used to measure sucrose.

A Class 4 example is oxalate decarboxylase, EC4.1.1.3, and splits oxalate into formate+$CO_2$. This enzyme, found in wood fungus, could measure oxalate by the release of $CO_2$. A transcutaneous $pCO_2$ electrode may be used to measure the $pCO_2$ which is related to the $CO_2$ by-product and hence the oxalate concentration. This enzyme does not require a co-factor.

Another Class 4 example is acetoacetate decarboxylase 4.1.1.10 which reacts with acetoacetate to give glycine+$CO_2$. This enzyme is found in liver. The acetoacetate is found in diabetes which is not properly controlled.

There are many other $CO_2$ producing enzymes such as:
Pyruvate decarboxylase EC4.1.1.1
Aspartate decarboxylase EC4.1.1.12
Glutamate decarboxylase EC4.1.1.13
Lysine decarboxylase EC4.1.1.18
Arginine decarboxylase EC4.1.1.19

In general, Class 5 enzymes could be used with oxygen oxidoreductases where the D-form of an enzyme was more stable than the L-form. For example, L-alamine could be converted to D-alamine so that it could be oxidized by D-amino acid oxidase.

An example in Class 6 is an enzyme (EC6.4.1.4) which uses $CO_2$ to convert 3-methylcrotonoyl CoA to 3-methylglutaconyl-CoA. These CoA compounds are panthethenic acid condensed with ADP and thioethanolamine and they play key roles in animal metabolism.

In performing the techniques of this invention, it should be understood that foreign or other proteins injected subcutaneously are absorbed rapidly. If glucose oxidase is injected subcutaneously it is absorbed. If the dose is high enough the animal may die because glucose is converted in part to $H_2O_2$ and this converts the hemoglobin to methemoglobin which does not carry oxygen. Proteolytic enzymes may destroy the enzyme or it may be picked up by Kupffer cells. If the immune system of the body including the opsonins can contact the enzyme, it will be marked for destruction. Some antibodies attach to enzymes (Freund's adjuvant is used to mix with the enzyme before injection) and they are inactivated by antibodies. In view of these observations, a preferred technique is to not let the enzymes escape and to not let immune proteins or macrophages contact the enzyme. The enzymes or co-enzymes could be placed in a containter such as a plastic bag or encapsulated in particles so that a substrate such as glucose can diffuse in, but protein molecules cannot permeate. Peroxide could be destroyed in the bag with catalase or allowed to diffuse out to be destroyed. Also, as developed above, the enzyme can be immobilized on an inert substrate such as nylon or silver. Glutaraldehyde treated tissues such as heart valves from other species have been used as substitute heart valves in human beings. Glutaraldehyde is also widely used to immobilize enzymes. Hence, glutaraldehyde can be used to immobilize and affix enzymes to surfaces for implantation where the probability of a rejection process would be very low. It is also recognized that monochromatic, dichromatic or multiplechromatic light can be transmitted through the earlobe and the light spectrum received on the other side to reveal the oxygen saturation of the blood. A transparent enzyme implant in the earlobe could be designed with an appropriate dye such that substrate concentration would be reflected by transmitted light.

As a result of enzyme reactions, fluorescence and phosphorescence can occur. Hence, by a suitable implant containing the enzyme and the photoactivated substance, one could detect substrate concentration by measuring the amount of light emitted to the skin by the phosphorescent reaction.

In view of the above description, other details and operating parameters will be obvious to a person of ordinary skill in this art.

I claim:

1. A non-invasive cutaneous method of analyzing body substrates in the body which comprises
    contacting in the body of non-gaseous body substrate with an enzyme selected for the substrate being analyzed,
    reacting the substrate with the enzyme, and
    detecting a condition of the skin without invading the body at the time of the detection as a measure of the amount of substrate in the body.

2. The method of claim 1 comprising placing an oxygen sensitive electrode in contact with the skin, reacting the substrate with an enzyme to produce a decrease in oxygen and detecting said oxygen decrease at the skin as a measure of the amount of substrate.

3. The method of claim 1 comprising locating the enzyme under the skin surface and detecting a condition of the enzymatic reaction at the skin as a measure of the amount of substrate.

4. The method of claim 1 comprising arterializing the skin.

5. The method of claim 4 wherein the skin is arterialized by heating.

6. The method of claim 5 wherein the skin is warmed to a temperature of about 38°–44° C.

7. The method of claim 4 wherein the skin is arterialized by chemical treatment.

8. The method of claim 1 comprising injecting the enzyme subcutaneously.

9. The method of claim 8 comprising mixing the enzyme with a material selected from the group consisting of silicone oil and fluorocarbon oil and injecting the mixture subcutaneously.

10. The method of claim 1 comprising subcutaneously implanting the enzyme.

11. The method of claim 10 comprising embedding the enzyme in a thin polymeric sheet and implanting through an incision in the skin.

12. The method of claim 10 comprising implanting a film containing an immobilized enzyme.

13. The method of claim 12 wherein the enzyme is immobilized by entrapment between two layers of a plastic film.

14. The method of claim 12 wherein the film comprises a polymer selected from the group consisting of cellophane, cupraphane, collagen and silicone polymer.

15. The method of claim 12 wherein enzyme is immobilized on the surface of the film by treating with gluteraldehyde solution and then drying.

16. The method of claim 1 comprising immobilizing the enzyme in a container which is selectively permeable for the substrate.

17. A non-invasive cutaneous method of extracorporeally analyzing blood substrates in the body of mammalian subjects which comprises
  transcutaneously contacting in the body a non-gaseous substrate with an enzyme selected for the substrate being analyzed,
  reacting the substrate with the enzyme,
  arterializing the skin, and
  detecting the condition of the skin without invading the body at the time of detection as a measure of the amount of substrate in the blood.

18. The method of claim 17 comprising placing the enzyme in a container under the skin which is selectively permeable for the substrate.

19. The method of claim 17 comprising detecting either oxygen decrease with an extracorporeal electrode as a measure of the amount of substrate.

20. An apparatus for non-invasively measuring body substrates in the body which comprises
  means for contacting in the body a non-gaseous body substrate with an enzyme selected for the substrate being analyzed and means for detecting a condition of the skin without invading the body at the time of the detection as a measure of the amount of substrate in the body.

21. The apparatus of claim 20 wherein the detecting means is a oxygen sensitive electrode.

22. The apparatus of claim 20 wherein said detection means is for direct contact with the skin.

23. The apparatus of claim 20 wherein the contacting means is for location under the surface of the skin.

24. The apparatus of claim 20 including means for arterializing the skin.

25. The apparatus of claim 24 comprising a heating element.

26. The apparatus of claim 25 wherein said element is operated at a temperature of about 38°–44° C.

27. The apparatus of claim 23 wherein the contacting means comprises an enzyme implant.

28. The apparatus of claim 27 wherein the enzyme implant comprises an enzyme embedded in a thin polymeric sheet.

29. The apparatus of claim 27 wherein the enzyme implant comprises a film containing an immobilized enzyme.

30. The apparatus of claim 29 wherein the enzyme is immobilized between two layers of a plastic film.

31. The apparatus of claim 30 wherein the film comprises a polymer selected from the group consisting of cellophane, cuprophane, collagen and silicone polymer.

32. The apparatus of claim 20 wherein the contacting means is a container having an immobilized enzyme therein and said container is selectively permeable for the substrate.

33. The apparatus of claim 20 comprising further means for vaporizing the substrate and wherein the detecting means is an extracorporeal device.

34. A detection device for analyzing body substrates in the body which comprises an enzyme immobilized in a layer for implantation in the body and for measurement of body substrates in the body without invading the body at the time of measurement while said enzyme layer is implanted.

35. The device of claim 34 wherein said enzyme is immobilized by being embedded in a thin polymeric sheet.

36. The device of claim 34 wherein the enzyme is immobilized between two layers of plastic film.

37. The device of claim 34 wherein the enzyme is immobilized within a container and said container being selectively permeable for the substrate.

* * * * *

UNITED STATES PATENT AND TRADEMARK OFFICE
CERTIFICATE OF CORRECTION

PATENT NO. : 4,401,122

DATED : August 30, 1983

INVENTOR(S) : Leland C. Clark, Jr.

Page 1 of 4

It is certified that error appears in the above-identified patent and that said Letters Patent is hereby corrected as shown below:

Col. 1, line 18, "p$CO_2$" should be --$CO_2$--

Col. 2, lines 25-26 "incoporating" should be --incorporating--

Col. 4, line 12 "emzyme" should be --enzyme--

Col. 6, line 32 after the word "invention." delete "t,0130"

Col. 6, after the paragraph ending on line 32, there should appear a TABLE as per the attached sheets.

Col. 8, line 55 "of" should be --a--

Signed and Sealed this

Seventeenth Day of July 1984

[SEAL]

Attest:

GERALD J. MOSSINGHOFF

Attesting Officer

Commissioner of Patents and Trademarks

TABLE

| Enzyme | Number | Source | Typical Substrates |
|---|---|---|---|
| Glycollate oxidase | 1.1.3.1 | spinach<br>rat liver | glycollate<br>L-lactate<br>D-lactate<br>(+)-mandalate |
| Lactate oxidase | 1.1.3.2 | M.phlei | L-lactate |
| Glucose oxidase | 1.1.3.4 | Aspergillus niger<br>Penicillium amagasakienses<br>honey (bee)<br>Penicillium notatum | β-D-glucose<br>2-dioxy-D-glucose<br>6-dioxy-6-fluoro-D-glucose<br>6-methyl-D-glucose |
| Hexose oxidase | 1.1.3.5 | | β-D-glucose<br>D-galactose<br>D-mannose |
| L-Gulonolactone oxidase | 1.1.3.8 | rat liver | L-gulono-λ-lactone<br>L-galactonolactono<br>D-manonolactone<br>D-altronolactone |
| Galactose oxidase | 1.1.3.9 | Dactylium dendroides,<br>Polyporus circinatus | D-galactose<br>stachyose<br>lactose |
| L-2-Hydroxyacid oxidase | 1.1.3.a | hog renal cortex | L-2-hydroxyacid |
| Aldehyde oxidase | 1.2.3.1 | rabbit liver<br>pig liver | formaldehyde<br>acetaldehyde |
| Xanthine oxidase | 1.2.3.2 | bovine milk<br>porcine liver | purine<br>hypoxanthine<br>benzaldehyde<br>xanthine |

TABLE (continued)

| Enzyme | Number | Source | Typical Substrates |
|---|---|---|---|
| Pyruvate oxidase | 1.2.3.3 | | pyruvate<br>requires thiamine phosphate |
| Oxalate oxidase | 1.2.3.4 | | oxalate |
| Dihydro-orotate-dehydrogenase | 1.3.3.1 | Zymobacterium oroticum | L-4, 5-dihydro-orotate<br>NAD |
| D-Aspartate oxidase | 1.4.3.1 | rabbit kidney | D-aspartate<br>D-glutamate |
| L-Amino-acid oxidase | 1.4.3.2 | diamond rattlesnake<br>cotton mouth moccasin<br>rat kidney | L-methionine<br>L-phenylalanine<br>2-hydroxy acids<br>L-lactate |
| D-Amino acid oxidase | 1.4.3.3 | hog kidney | D-alanine<br>D-valine<br>D-proline |
| Monoamine oxidase | 1.4.3.4 | beef plasma<br>placenta | monoamine<br>benzylamine<br>octylamine |
| Pyridoxamine phosphate oxidase | 1.4.3.5 | rabbit liver | pyridoxamine phosphate |
| Diamine oxidase | 1.4.3.6 | bovine plasma<br>pea seedlings<br>procine plasma | diamines<br>spermidine<br>tyramine |
| Sarcosine oxidase | 1.5.3.1 | Macaca mulatta<br>rat liver metochondria | sarcosine |

TABLE (continued)

| Enzyme | Number | Source | Typical Substrates |
|---|---|---|---|
| N-Methyl-L-amino acid oxidase | 1.5.3.2 | | N-methyl-L-amino acids |
| Spermine oxidase | 1.5.3.3 | *Neisseria perflava* *Serratia marcescens* | spermine spermidine |
| Nitroethane oxidase | 1.7.3.1 | | nitroethane aliphatic nitro compounds |
| Urate oxidase | 1.7.3.3 | hog liver ox kidney | urate |
| Sulfite oxidase | | beef liver | sulfite |
| Alcohol oxidase | 1.8.3.1 | Basidiomycetes | ethanol and methanol |
| Carbohydrate oxidase | | Basidiomycetes *Polyporus obtusus* | D-glucose D-glucopyranose D-xylopyranose l-sorbose $d$-D-gluconolactone |
| NADH oxidase | | beef heart mitochondria | NADH |
| Malate oxidase | 1.1.3.2 | | L-malate |
| Cholesterol oxidase | 1.1.3.6 | | cholesterol |
| N-Acetylindoxyl oxidase | 1.7.3.2 | | N-acetylindoxyl |
| Thiol oxidase | 1.8.3.2 | | R: CR-SH |
| Ascorbate oxidase | 1.10.3.3 | squash | L-ascorbate |